(12) United States Patent
Kamiyama

(10) Patent No.: US 8,360,980 B2
(45) Date of Patent: Jan. 29, 2013

(54) ULTRASONIC DIAGNOSIS APPARATUS AND ULTRASONIC DIAGNOSIS APPARATUS CONTROL METHOD

(75) Inventor: Naohisa Kamiyama, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 158 days.

(21) Appl. No.: 11/064,096

(22) Filed: Feb. 24, 2005

(65) Prior Publication Data

US 2005/0203406 A1 Sep. 15, 2005

(30) Foreign Application Priority Data

Feb. 27, 2004 (JP) ................................. 2004-053135

(51) Int. Cl.
*A61B 8/00* (2006.01)
(52) U.S. Cl. ........................................ 600/458; 600/437
(58) Field of Classification Search .................. 600/458, 600/437
See application file for complete search history.

(56) References Cited

U.S. PATENT DOCUMENTS

| | | | |
|---|---|---|---|
| 5,694,937 A | 12/1997 | Kamiyama | |
| 5,833,613 A | 11/1998 | Averkiou et al. | |
| 5,860,931 A * | 1/1999 | Chandler | 600/458 |
| 5,944,666 A * | 8/1999 | Hossack et al. | 600/458 |
| 6,149,597 A | 11/2000 | Kamiyama | |
| 6,174,287 B1 | 1/2001 | Resnick et al. | |
| 6,245,019 B1 | 6/2001 | Kamiyama | |
| 6,464,644 B2 | 10/2002 | Hashimoto | |
| 6,575,910 B2 * | 6/2003 | Averkiou et al. | 600/458 |
| 2002/0165455 A1 | 11/2002 | Lysyansky | |
| 2003/0229285 A1 | 12/2003 | Simpson et al. | |

FOREIGN PATENT DOCUMENTS

| | | |
|---|---|---|
| EP | 1 314 398 A1 | 5/2003 |
| JP | 11-155858 | 6/1999 |
| JP | 11-318901 | 11/1999 |
| JP | 2001-252270 | 9/2001 |
| WO | WO 03/103497 A1 | 12/2003 |

OTHER PUBLICATIONS

U.S. Appl. No. 11/280,326, filed Nov. 17, 2005, Yoshida et al.
U.S. Appl. No. 12/237,683, filed Sep. 25, 2008, Kamiyama et al.

* cited by examiner

*Primary Examiner* — Jacqueline Cheng
(74) *Attorney, Agent, or Firm* — Oblon, Spivak, McClelland, Maier & Neustadt, L.L.P.

(57) ABSTRACT

After executing a second transmission constituting an ultrasonic wave of an amount of one frame from an ultrasonic wave having a high sound pressure of destructing bubbles in a predetermined section for making a blood stream image or a tissue image in a circulation image of a blood stream disappear by making the bubbles in the predetermined section disappear, there is carried out a third transmission by an ultrasonic wave having a low sound pressure of not substantially destructing the bubbles for acquiring the circulation image of the blood stream with regard to the predetermined section. The first transmission is executed by the ultrasonic wave for making a portion of the blood stream image in the circulation image disappear by making the bubbles at the predetermined region present in the predetermined section disappear as necessary while executing the third transmission.

17 Claims, 10 Drawing Sheets

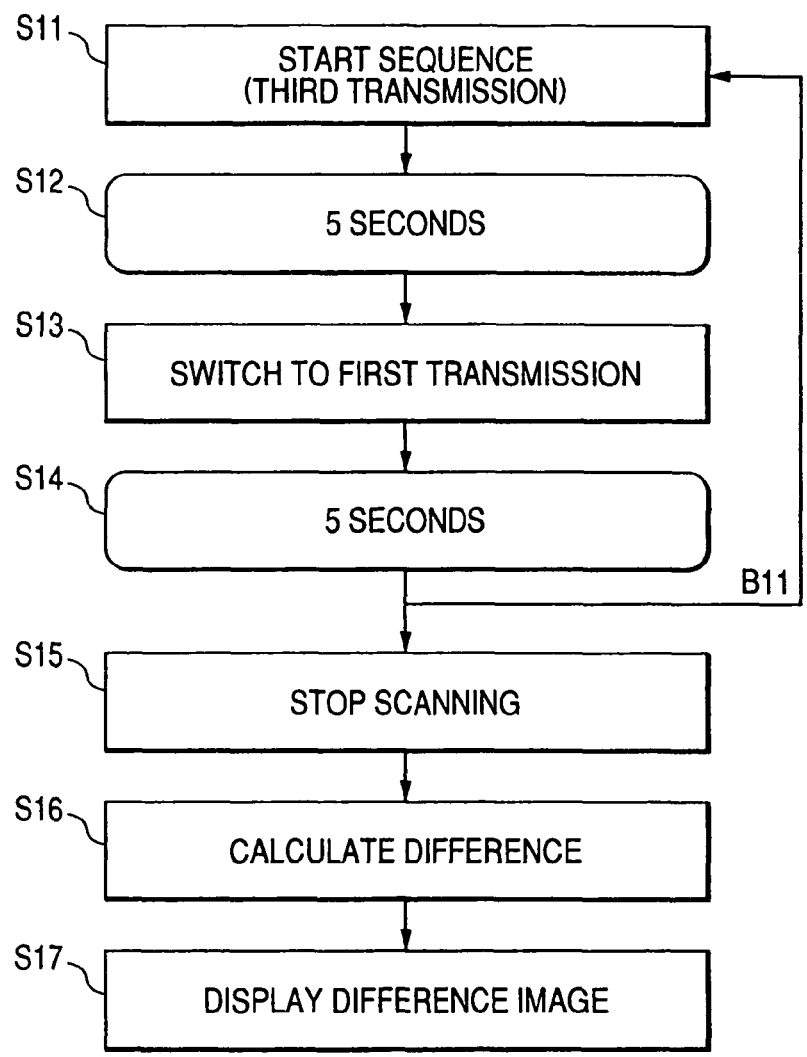

ULTRASONIC DIAGNOSIS APPARATUS AND ULTRASONIC DIAGNOSIS APPARATUS CONTROL METHOD

CROSS-REFERENCE TO RELATED APPLICATIONS

This application is based upon and claims the benefit of priority from prior Japanese Patent Application No. 2004-053135, filed Feb. 27, 2004, the entire contents of which are incorporated herein by reference.

BACKGROUND OF THE INVENTION

1. Field of the Invention

The present invention relates to an ultrasonic diagnosis apparatus, an image processing apparatus and an ultrasonic image taking method capable of presenting fine structures of a fine circulating blood stream at a capillary level and a blood vessel stream which is comparatively faster than that of a capillary in an imaging echo method executed by using an ultrasonic contrast medium as diagnosis information.

2. Description of the Related Art

According to an ultrasonic diagnosis, beat of the heart or a moving behavior of the embryo is provided by a real time display by a simple operation of only touching an ultrasonic probe from the body surface, inspection can be carried out repeatedly since the safety is high and a scale of a system is smaller than that of other diagnosis apparatus of X-ray, CT, MRI or the like and inspection can also be executed easily by moving to a bed side, which is convenient.

Further, although an ultrasonic diagnosis apparatus differs variously depending on kinds of functions provided thereto, a small-sized apparatus being able to carried by one hand has been developed and can be used at a maternity clinic or in a medical treatment at home without being influenced by exposure as in X-ray or the like in the ultrasonic diagnosis.

In recent years, an intravenous administration type ultrasonic contrast medium has been produced and an imaging echo method has been carried out. It is an object of the method to evaluate a dynamic flow behavior by intensifying a blood stream signal by is injecting an ultrasonic contrast medium from the vein in inspecting, for example, the heart or the lever. In a number of ultrasonic contrast media, micro bubbles function as a reflection source. In view of a property of a delicate member of bubble, even by ultrasonic irradiation at a normal diagnosis level, bubbles are suppressed by mechanical operation thereof, as a result, a signal intensity from a scanning face is reduced. Therefore, in order to observe a dynamic behavior of a circulating flow in real time, it is necessary to comparatively reduce collapse of bubbles by scanning such that imaging is carried out by ultrasonic transmission at a low sound pressure. Such an imaging by ultrasonic transmission at the low sound pressure also reduces a signal/noise ratio (S/N ratio) and therefore, there have been devised various signal processing methods to supplement therefor.

Further, the following method has been devised in, for example, JP-A-11-155858 by making full use of the above-described collapsing characteristic of bubbles of contrast media. That is, this is a method of A observing a dynamic behavior of bubbles filling a scanning section under irradiation at a low sound pressure, B suppressing bubbles in the section (strictly, in an irradiated volume) by switching the irradiated sound pressure to a high sound pressure, and C observing a behavior of bubbles flowing again into the section. The method is referred to as a replenishment method.

Meanwhile, generally, although when the blood vessel constructed in the organ of the living body is comparatively bold, a structure thereof is easy to grasp, in the case of illustrating even the finer branch by imaging echo, an image of complicatedly entwining the blood vessels is illustrated. Since the current ultrasonic contrast media are of a low invasive intravenous administration type, the media circulate the whole body. Therefore, it has been conceived in the ultrasonic diagnosis that an image as in selective image of the blood vessel in X-ray using a catheter cannot be provided.

However, it seems that bubbles can selectively be made to disappear by utilizing the above-described property of bubbles. Further, it is clinically much significant to be able to provide a diagnosis image as in imaging by X-ray in an ultrasonic image diagnosis by establishing such a method.

BRIEF SUMMARY OF THE INVENTION

The invention has been carried out in view of the above-described situation and it is an object thereof to provide an ultrasonic diagnosis apparatus and an ultrasonic diagnosis apparatus control method capable of selectively illustrating diagnosis information at a fine blood vessel branch level.

According to an aspect of the present invention, there is provided an ultrasonic diagnosis apparatus for acquiring an ultrasonic image by scanning a predetermined portion of a subject administered with bubbles of a contrast medium by an ultrasonic wave, the ultrasonic diagnosis apparatus comprising: an ultrasonic probe for transmitting the ultrasonic wave to the subject and receiving an echo signal from the subject; a signal generating unit for generating a drive signal for driving the ultrasonic probe; and a controller for controlling the drive signal generating unit to execute a scan of a section by repeating a first ultrasonic wave transmission including an ultrasonic wave having a sound pressure to a degree of not substantially destructing the bubbles of the contrast medium for acquiring a circulation image of a blood stream with regard to a predetermined section and an ultrasonic wave having a sound pressure to a degree of destructing the bubbles of the contrast medium for destructing the bubbles of the contrast medium at part of a desired blood vessel and restraining the contrast medium from flowing into the desired blood vessel.

According to another aspect of the present invention, there is provided an ultrasonic diagnosis apparatus for acquiring an ultrasonic wave image by scanning a predetermined portion of a subject administered with bubbles of a contrast medium by an ultrasonic wave, the ultrasonic diagnosis apparatus comprising: an ultrasonic probe for transmitting the ultrasonic wave to a transmitted region of the subject and receiving an echo signal from the subject; a signal generating unit for generating a drive signal for driving the ultrasonic probe; and a controller for controlling the signal generating unit to repeatedly execute an ultrasonic wave transmission having a sound pressure to a degree of not substantially destructing the bubbles of the contrast medium for acquiring a circulation image of a blood stream with regard to the transmitted region and an ultrasonic wave transmission for making the bubbles of the contrast medium present at least a portion of the transmitted region disappear by a sound pressure to a degree of destructing the bubbles of the contrast medium to restrain the contrast medium from flowing into a desired blood vessel.

According to another aspect of the present invention, there is provided a method of controlling an ultrasonic diagnosis apparatus for acquiring an ultrasonic wave image by scanning a predetermined portion of a subject administered with bubbles of a contrast medium by an ultrasonic wave, the method comprising the steps of: generating a drive signal for driving an ultrasonic probe for transmitting the ultrasonic wave to the subject and receiving an echo signal from the subject; and controlling the drive signal generating unit to execute by a plurality of times a first ultrasonic wave transmission constituting an ultrasonic wave of an amount of one frame from an ultrasonic wave having a sound pressure to a degree of not substantially destructing the bubbles of the contrast medium for acquiring a circulation image of a blood stream with regard to a predetermined section and an ultrasonic wave having a sound pressure to a degree of destructing the bubbles of the contrast medium for making at least a portion of the bubbles of the contrast medium present at the predetermined section disappear and restraining the contrast medium from flowing into a desired blood vessel.

According to another aspect of the present invention, there is provided a method of controlling an ultrasonic diagnosis apparatus for acquiring an ultrasonic wave image by scanning a predetermined portion of a subject administered with bubbles of a contrast medium by an ultrasonic wave, the method comprising the steps of: generating a drive signal for driving an ultrasonic probe for transmitting the ultrasonic wave to a transmitted region of the subject and receiving an echo signal from the subject; and controlling the signal generating unit to repeatedly execute an ultrasonic wave transmission having a sound pressure to a degree of not substantially destructing the bubbles of the contrast medium for acquiring a circulation image of a blood stream with regard to the transmitted region and an ultrasonic wave transmission for making the bubbles of the contrast medium present at least a portion of the transmitted region disappear by a sound pressure to a degree of destructing the bubbles of the contrast medium to restrain the contrast medium from flowing into a desired blood vessel.

BRIEF DESCRIPTION OF THE SEVERAL VIEWS OF THE DRAWING

FIG. 6 is a flowchart showing a flow of respective processings executed by the ultrasonic diagnosis apparatus 10 in accordance with a scan sequence according to a second embodiment;

DETAILED DESCRIPTION OF THE INVENTION

An explanation will be given of a first through a third embodiment of the invention in reference to the drawings as follows. Further, in the following explanation, constituent elements having substantially the same functions and constitutions are attached with the same notations and a duplicated explanation thereof will be given only when needed.

First Embodiment

Figure 1:
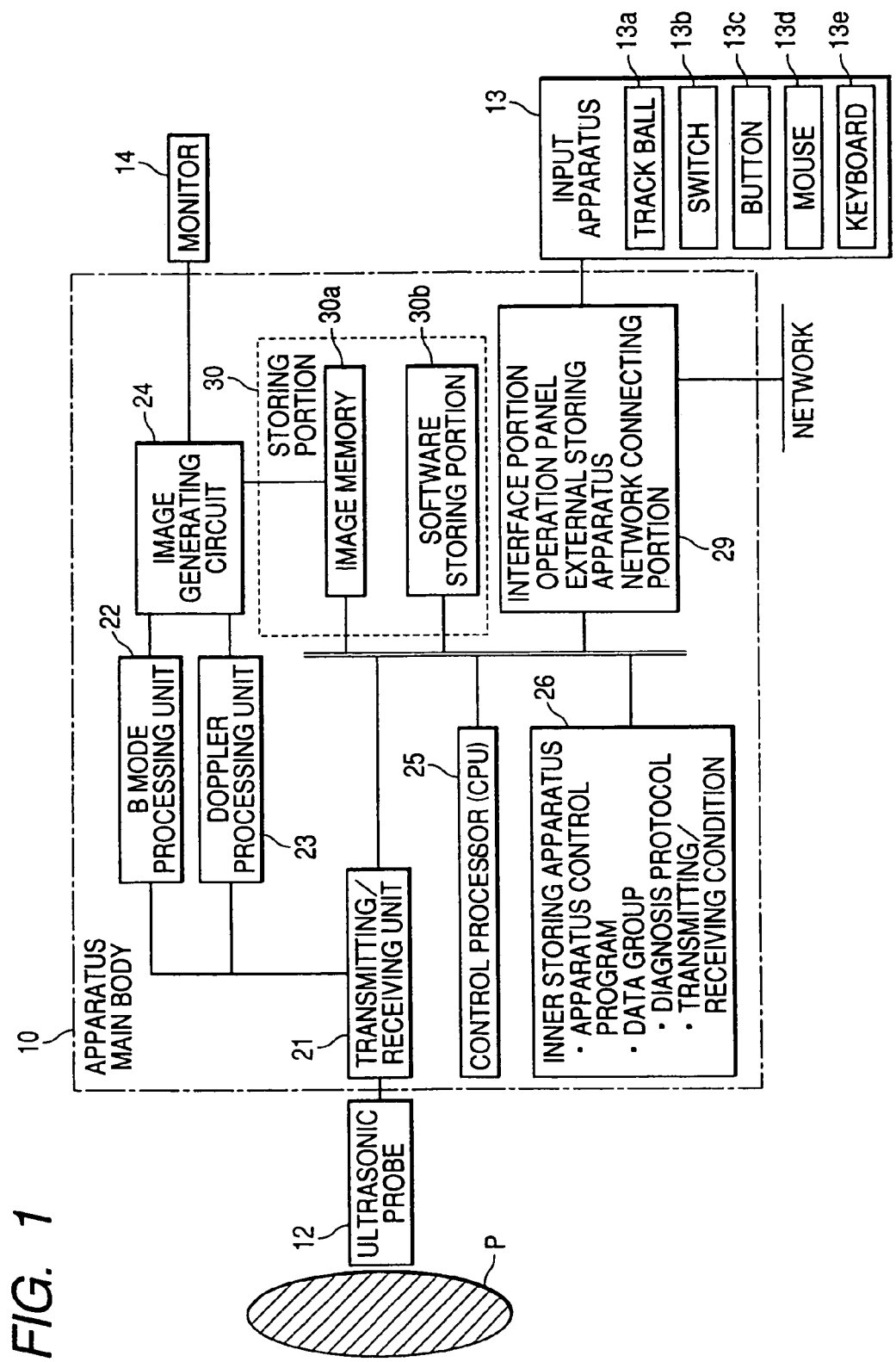
FIG. 1 is a diagram showing a block constitution of an ultrasonic diagnosis apparatus 10 according to an embodiment.

FIG. 1 is a diagram showing a block constitution of an ultrasonic diagnosis apparatus 10 according to the embodiment. As shown by the drawing, the ultrasonic diagnosis apparatus 10 is provided with an ultrasonic probe 12, an input apparatus 13, a monitor 14, a transmitting/receiving unit 21, a B mode processing unit 22, a Doppler processing unit 23, an image generating circuit 24, a control processor 25, an inner storing apparatus 26, an image memory 27, an interface portion 29, and a storing portion 30 including an image memory 30a and a software storing portion 30b. Although there is a case in which the ultrasonic transmitting/receiving unit 21 and the like included in an apparatus main body 11 is constituted by a hardware of an integrated circuit or the like, there is also a case in which the ultrasonic transmitting/receiving unit and the like are constituted by a software program moduled in the form of softwares. An explanation will be given of functions of individual constituent elements as follows.

The ultrasonic probe 12 includes a plurality of piezoelectric oscillators for generating an ultrasonic wave based on a drive signal from the ultrasonic transmitting/receiving unit 21 and converting a reflected wave from a subject into an electric signal, an acoustic matching layer provided to the piezoelectric oscillator, and a backing member for preventing an ultrasonic wave from being propagated rearward from the piezoelectric oscillator. When an ultrasonic wave is transmitted from the ultrasonic probe 12 to the subject P, the transmitted ultrasonic wave is reflected successively by a discontinuous face of an acoustic impedance of the internal tissue and is received by the ultrasonic probe 12 as an echo signal. An amplitude of the echo signal depends on a difference in the acoustic impedance at the discontinuous face at which the ultrasonic wave is reflected. Further, when the transmitted ultrasonic pulse is reflected by a moving blood stream or a surface of the heart wall or the like, an echo depends on a velocity component in a direction of transmitting the ultrasonic wave to the moving body by Doppler's effect to receive a deviation in a frequency.

The input apparatus 13 includes a track ball 13a, various switches 13b, a button 13c, a mouse 13d, a keyboard 13e and the like connected to the apparatus main body 11 for inputting various instructions from an operator, settings and instructions of conditions, regions of interest (ROI), settings and instructions of various image quality conditions and the like.

The monitor 14 displays morphological information in the living body, or blood stream information based on a video signal from the image generating circuit 24.

The transmitting/receiving unit 21 includes a trigger generating circuit, a delay circuit and a pulser circuit, not illustrated. At the pulser circuit, a rate pulse for forming a transmitting ultrasonic wave is repeatedly generated at a predetermined rate frequency fr Hz (period; 1/fr second). Further, at the delay circuit, each rate pulse is provided with a delay time period necessary for focusing the ultrasonic wave in a beam-like shape and determining transmission directivity for each channel. The trigger generating circuit applies a drive pulse to the probe 12 at a timing based on the rate pulse.

Further, the transmitting/receiving unit 21 is provided with a function of capable of instantaneously changing a transmitting frequency or a transmitting drive voltage for executing a scan sequence, mentioned later, in accordance with an instruction from the control processor 25. Particularly, a change in the transmitting drive voltage is realized by a transmitting circuit of a linear amplifier type capable of instantaneously switching a value of the transmitting drive voltage, or a mechanism of electrically switching a plurality of power source units.

Further, the transmitting/receiving unit 21 includes an amplifier circuit, an A/D converter and an adder, not illustrated. The amplifier circuit amplifies the echo signal inputted via the probe 12 for each channel. The A/D converter provides a delay time period necessary for determining reception directivity for the amplified echo signal, thereafter, an addition processing is executed at the adder. By the addition, a reflection component from the direction in accordance with the reception directivity of the echo signal is emphasized and a general beam of transmitting and receiving the ultrasonic wave is formed by the reception directivity and the transmission directivity.

The B mode processing unit 22 receives the echo signal from the transmitting/receiving unit 21 to subject to logarithmic amplification or envelope detection processing and generates data representing a signal intensity by brightness. The data is transmitted to the image generating circuit 24 and is displayed on the monitor 14 as a B mode image representing the intensity of the reflected wave by the brightness.

The Doppler processing unit 23 subjects the echo signal received from the transmitting/receiving unit 21 to frequency analysis to derive velocity information, extracts echo components of the blood stream, the tissue or the contrast medium by the Doppler's effect and calculates blood stream information of mean velocity, dispersion or power at a number of points. The provided blood stream information is transmitted to the image generating circuit 24 and is displayed on the monitor 14 in color as an image of the mean velocity, an image of the dispersion, an image of the power, or an image combined with these.

The image generating circuit 24 converts a scanning line signal row of ultrasonic scan into a scanning line signal row of a general video format represented by television or the like and generates an ultrasonic diagnosis image as a display image. The image generating circuit 24 is mounted with a storage memory for storing image data, and is made to be able to call an image recorded in inspection by the operator after, for example, the diagnosis. Further, data before being brought into the image generating circuit 24 may be referred to as "live data".

Figure 2:
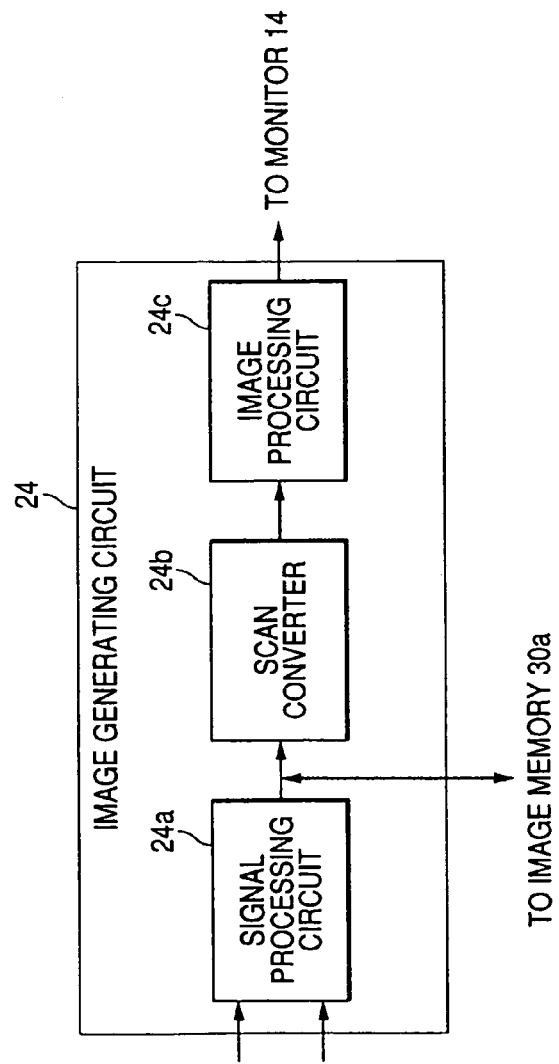
FIG. 2 is a diagram showing a constitution of an image generating circuit 24.

FIG. 2 shows details of the image generating circuit 24. First, a signal processing circuit 24a executes filtering for determining an image quality at a level of the scanning line signal row of the ultrasonic scan. An output of the signal processing circuit 24a is transmitted to a scan converter 24b and is preserved in the image memory 30a simultaneously therewith. The scan converter 24b converts the scanning line signal row of the ultrasonic scan into the scanning line signal row of the general video format represented by television. An output thereof is transmitted to an image processing circuit 24c, where the output is subjected to adjustment of a brightness or a contrast, an image processing of space filter or the like, or synthesized with character information or graduation of various set parameters and is outputted to the monitor 14 as a video signal. In this way, a tomographic image representing a shape of the tissue of the subject is displayed.

The control processor (CPU) 25 is provided with a function as an information processing apparatus (computer) and is control means for controlling operation of the ultrasonic diagnosis apparatus main body. The control processor 25 reads a control program for executing to transmit and receive an ultrasonic wave, generate and display an image, mentioned later, from the inner storing apparatus 26 to develop on the software storing portion 30b and executes operation and control with regard to various processings.

The inner storing apparatus 26 is stored with control programs for executing a scan sequence, an image forming and a display processing, and data groups of diagnosis information (patient ID, finding of doctor), diagnosis protocol, transmitting/receiving conditions and the like. Particularly, the inner storing apparatus 26 is stored with control programs for executing a scan sequence for transmitting and receiving an ultrasonic wave, mentioned later, a processing of generating a difference image, and operational processing of holding a brightness, a superposed display, or a display of a third transmission object region. Further, the inner storing apparatus 26 is used also for storing an image in the image memory 30a as necessary. Data of the inner storing apparatus 26 can also be transmitted to an external peripheral apparatus via the interface circuit 30.

The interface portion 29 is an interface with regard to the input apparatus 13, a network, or a new external storing apparatus (not illustrated). Data of an ultrasonic image or a result of analysis provided by the apparatus can be transmitted to other apparatus via the network by the interface portion 29. Further, the interface portion 29 is provided with a button exclusive for making a first transmission, mentioned later, ON/OFF. By operating the exclusive button, the first transmission can be made to ON/OFF at an arbitrary timing. By making the exclusive button ON/OFF, an image of restraining the contrast medium from flowing in and an image of making the contrast medium flowing in can be switched to display.

The image memory 30a comprises a storage memory for storing image data received from the signal processing circuit 24a. The image data is made to be able to call by the operator after, for example, diagnosis and can reproduce a static image or a dynamic image using a plurality of sheets thereof. Further, the image memory 30a is stored with an output signal (referred to as radio frequency (RF) signal) immediately after the ultrasonic transmitting/receiving unit 21, an image brightness signal after passing the transmitting/receiving unit 21, other live data, or the image data acquired via a network as necessary.

(Characteristics of Various Ultrasonic Transmissions)

The ultrasonic diagnosis apparatus 10 executes three kinds of ultrasonic transmissions of a first transmission, a second transmission and a third transmission under control of the control processor 25. Each property of ultrasonic transmissions will be described hereinbelow.

The second transmission is a transmission of an ultrasonic wave having a high sound pressure to a degree of collapsing bubbles of a contrast medium in a scanning face in contrast echo using the contrast medium. The third transmission is a transmission of an ultrasonic wave having a low sound pressure to a degree of capable of acquiring a diagnosis image by collapsing bubbles in the scanning face as less as possible. The first transmission is a transmission executed by constituting an object of collapsing bubbles (or restraining the contrast medium from flowing in) at least a portion in the scanning face and a transmission constituting an ultrasonic wave of an amount of one frame from, for example, an ultrasonic wave having a low sound pressure to a degree of capable of acquiring the diagnosis image by collapsing bubbles in the scanning face as less as possible and an ultrasonic wave having a high sound pressure to a degree of collapsing bubbles of the contrast medium in the scanning face. In the first transmission, a region constituting an object of irradiating an ultrasonic wave having a high sound pressure to a degree of collapsing bubbles of the contrast medium may be a region in a circular arc shape or the like or a region of a scanning line.

Figure 3A:
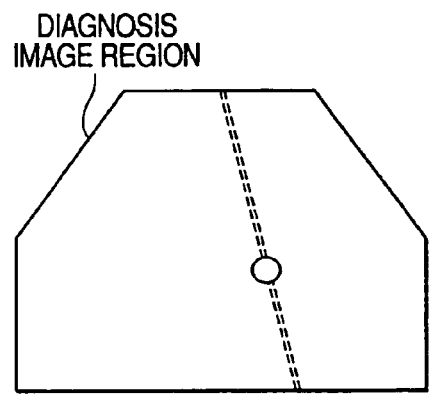
FIG. 3A through FIG. 3C are views showing a region constituting an object of a third transmission and display examples of the region.
Figure 3B:
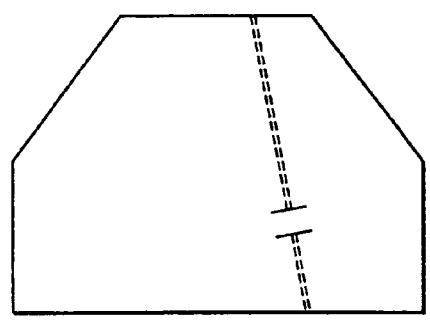
Figure 3C:
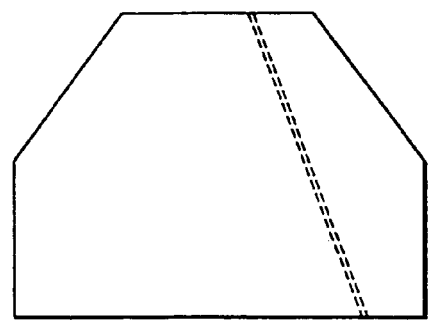

The above-described region of executing the first transmission is displayed on the monitor 14 by a predetermined mode. FIG. 3A through FIG. 3C are views showing a region constituting an object of irradiating an ultrasonic wave having a high sound pressure by the first transmission (region of irradiating the ultrasonic wave having the high sound pressure by the first transmission) and display examples of the region. FIG. 3A shows an irradiating direction by a line and shows a region of the highest sound pressure of a sound field of a focused ultrasonic wave by a circle. FIG. 3B shows the irradiating direction and the region of the highest sound pressure both by lines. The region constituting the object of irradiating the ultrasonic wave having the high sound pressure can be set to an arbitrary position by the operator by operating the input apparatus 13.

Meanwhile, the ultrasonic pulse is irradiated from a face of a prove oscillator having a limited size and therefore, strictly speaking, it is difficult to provide the high sound pressure only at a very small region. Hence, actually, simply, there is also a method of showing a scanning line of irradiating the high sound pressure only by a line.

(Scan Sequence)

Next, an explanation will be given of a basic scan sequence executed by the ultrasonic diagnosis apparatus 10. Further, a contrast medium preferable for being used in imaging in accordance with the sequence is referred to as so-to-speak "next generation contrast medium" capable of executing imaging for a long period of time by emitting a harmonic signal without being destructed even when an ultrasonic wave having a low sound pressure is transmitted thereto. Further, when a small amount and a constant amount of the contrast medium is administered, a concentration of the contrast medium in the body can be maintained constant for a comparatively long period of time, which is preferable for a method according to the embodiment.

Figure 4:
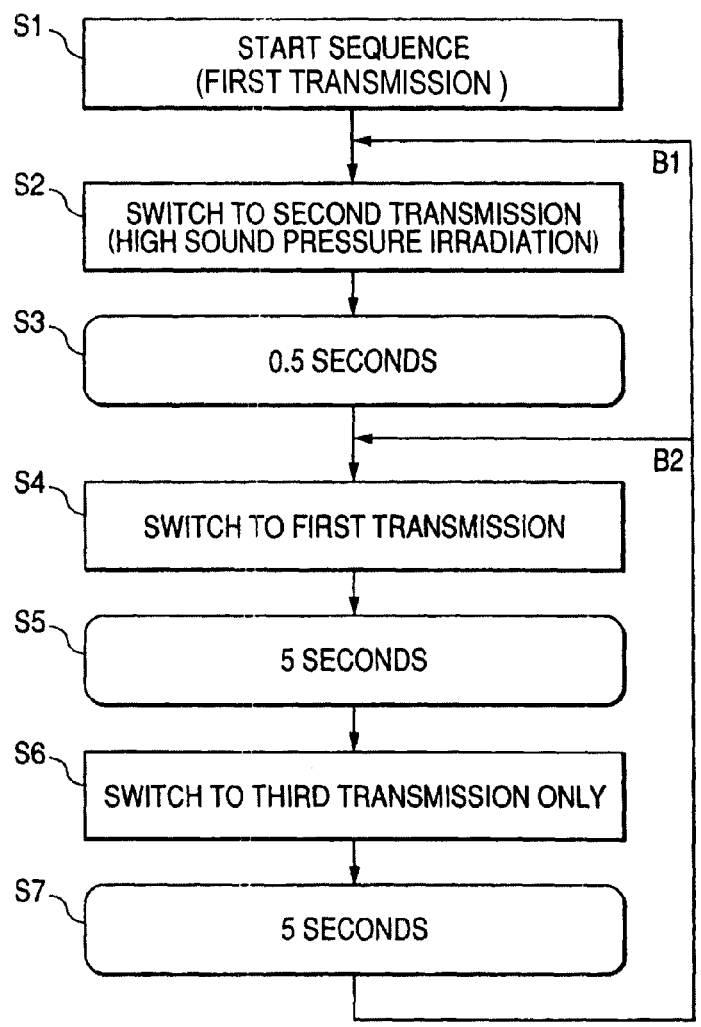
FIG. 4 is a flowchart showing a flow of respective processings executed by the ultrasonic diagnosis apparatus 10 in accordance with a scan sequence according to a first embodiment.

FIG. 4 is a flowchart showing a flow of respective processings executed by the ultrasonic wave diagnosis apparatus 10 in accordance with the scan sequence.

First, parameters necessary for executing the diagnosis sequence are set and the sequence is started by the operator (step S1). The parameters necessary for the diagnosis sequence are, for example, a region of irradiating the ultrasonic wave having the high pressure by the first transmission, a time period of transmitting the first transmission (first transmission time period), a time period of transmitting the second transmission (second transmission time period), and a time period of transmitting the third transmission (third transmission time period). Here, the first transmission time period is set to 5 seconds, the second transmission time period is set to 0.5 seconds, the third transmission time period is set to 5 seconds and the region of irradiating the ultrasonic wave high sound pressure by the first transmission is set to the trunk portion of the predetermined blood vessel.

Figure 5A:
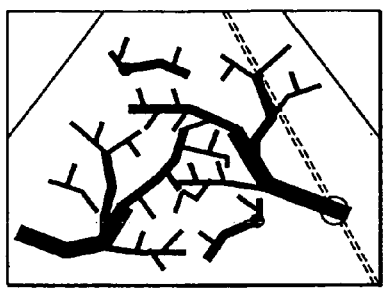
FIG. 5A through FIG. 5D are views schematically showing images provided by ultrasonic transmission and reception in accordance with the scan sequence according to the first embodiment.

Further, in setting the region of irradiating the ultrasonic wave having the high pressure by the first transmission, illustration of the blood vessel by the contrast medium has already been executed. Therefore, as shown by FIG. 5A, it is possible to pay attention to the single blood vessel on the illustrated image of the blood vessel and set an irradiating region at the trunk portion of the blood vessel on the image by the predetermine input apparatus.

Next, the first transmission is switched to the second transmission by the ultrasonic wave having the high sound pressure to the degree of collapsing bubbles of the contrast medium (step S2), and the second transmission is executed for 0.5 seconds in accordance with the transmission time period set at step S1 (step S3).

Figure 5B:
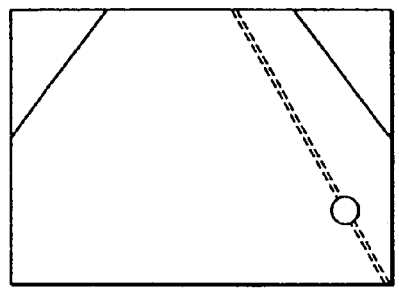

Next, after executing the second transmission for 0.5 seconds, the second transmission is switched to the first transmission (step S4). Further, by the second transmission, almost all the bubbles of the contrast medium in the scanning face are destructed. Therefore, immediately after switching the transmission, as shown by FIG. 5B, bubbles of the contrast medium are hardly observed to flow in and an image in which bubbles of the contrast medium are wiped out and the blood vessel or the like which is not imaged is displayed on the monitor 14.

Figure 5C:
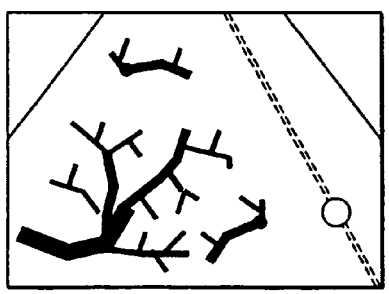

Next, the first transmission is executed for 5 seconds (set value at step S1 by operator) and a diagnosis image provided thereby is displayed in real time (step S5). At this stage, bubbles of the contrast medium are stopped to supply at a region of focusing the ultrasonic wave having the high pressure in the first transmission (the region of irradiating the ultrasonic wave having the high pressure in the first transmission). Therefore, according to the displayed diagnosis image, as shown by FIG. 5C, blood stream information present outside of the region of irradiating the ultrasonic wave having the high pressure by the first transmission is illustrated.

Figure 5D:
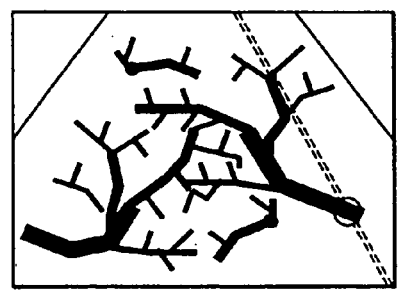

Next, the first transmission is switched only to the third transmission by the ultrasonic wave having the low sound pressure to a degree of capable of acquiring the diagnosis image by collapsing bubbles as less as possible (step S6), the third transmission is executed for 5 seconds (set value at step S1 by operator), and the diagnosis image provided thereby is displayed in real time (step S7). According to the diagnosis image at the stage, as shown by FIG. 5D, the blood stream information is illustrated over an entire region of the tomographic face.

Further, the time intervals at step S5, S7 can also be switched at an arbitrary timing by inputting to switch the button by the operator without setting the time intervals beforehand.

Next, the operator finishes a series of the sequence by repeating processings from step S2 (branch B1) or step S4 (branch B2) by executing a predetermined processing as necessary.

According to the above-described sequence, at step S7, a signal from the blood vessel to which bubbles have been stopped to supply there before is increased. Therefore, by the dynamic image reaching FIG. 5D from FIG. 5C, illustration of the blood vessel by increasing the signal can selectively be observed and it can easily be known how the blood stream from the blood vessel to which attention is paid presents a dynamic blood behavior.

Further, by repeating the first transmission as necessary, only the blood vessel to which attention is paid in the image can selectively be eliminated and by switching to the third transmission thereafter, the dynamic blood behavior with regard to the blood vessel to which attention is paid can be confirmed again at an arbitrary timing.

Further, by executing the second transmission as necessary, the image of the blood vessel present in the image can be eliminated at an arbitrary timing and by switching to the first transmission or the third transmission thereafter, the desired dynamic blood behavior with regard to the blood vessel can be confirmed at an arbitrary timing.

Second Embodiment

Next, an explanation will be given of a second embodiment of the invention. According to the second embodiment, only an image with regard to the blood vessel to which attention is paid is taken out by executing a predetermined image processing.

FIG. 6 is a flowchart showing a flow of respective processings executed by the ultrasonic diagnosis apparatus 10 in accordance with a scan sequence according to the embodiment.

First, as shown by FIG. 6, parameters necessary for executing the diagnosis sequence are set and the sequence is started by the operator (step S11). The parameters necessary for the diagnosis sequence are, for example, the first transmission time period, the region of irradiating the ultrasonic wave having the high pressure by the first transmission, and the third transmission time period. Here, the third transmission time period is set to 5 seconds, the first transmission time period is set to 5 seconds, and the region of irradiating the ultrasonic wave having the high pressure by the first transmission is set to the trunk portion of the predetermined blood vessel as shown by FIG. 6A.

Next, the third transmission is executed for 5 seconds (set value at step S11 by the operator) and the diagnosis image provided thereby is displayed in real time (step S12).

Next, the third transmission is switched to the first transmission (step S13) and irradiation of the ultrasonic wave for 5 seconds (set value at step S1) by the operator is executed, and the diagnosis image provided thereby is displayed in real time (step S14). According to the diagnosis image at this stage, bubbles of the contrast medium are stopped to supply to the region of irradiating the ultrasonic wave having the high pressure by the first transmission. Therefore, according to the displayed diagnosis image, as shown by FIG. 7B, the blood flow information present outside of the irradiating region is illustrated.

Further, at the stage of finishing the processing at step S14, the operator can return to step S11 as shown by branch B11 and acquire the image of the third transmission again as necessary.

When the diagnosis image by the third transmission and the diagnosis image by the first transmission are acquired as described above, the operator stops scanning by operating a "scan freeze button" or the like (step S15).

Figure 8A:
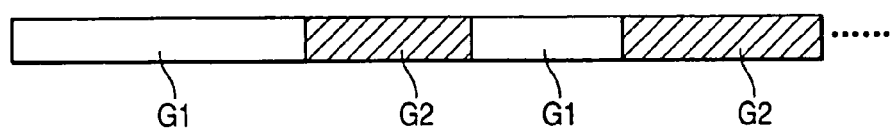
FIG. 8A is a diagram conceptually showing an image time-sequentially recorded in an image memory and FIG. 8B illustrates views showing ultrasonic images displayed by being divided in two based on the image time-sequentially recorded in the image memory.
Figure 8B:
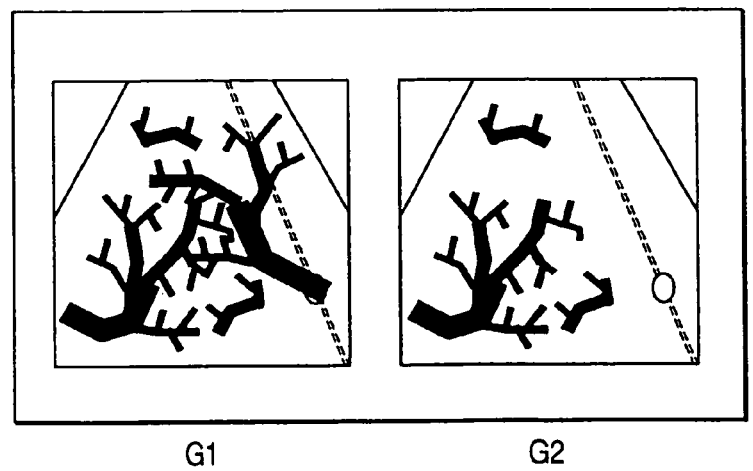

Further, at this occasion, an identifying code of whether the image recorded in the image memory 30a is the image by the third transmission or the image by the first transmission is recorded in header information of the image. Thereby, with regard to a group of images normally recorded time-sequentially as in a schematic view shown in, for example, FIG. 8A, at the display portion, as shown by FIG. 8B, a two-divided display mode can be adopted, it can selectively be displayed such that, for example, an image group G1 by the third transmission is displayed on the left side of the screen and an image group G2 by the first transmission is displayed on the right side of the screen.

Next, when pertinent images are selected respectively from the image groups of G1, G2 by utilizing the above-described display mode, from a pixel brightness value of the image G1, a pixel brightness value of the image G2 spatially in correspondence therewith is subtracted and a difference image is generated (step S16).

Figure 7A:
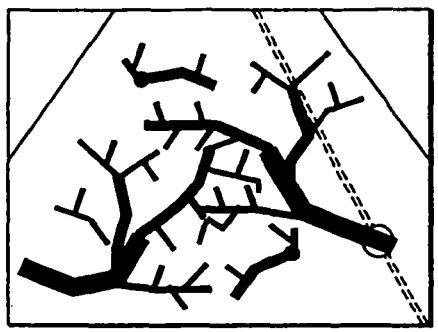
FIG. 7A through FIG. 7C are views schematically showing images provided by ultrasonic transmission and reception in accordance with the scan sequence according to the second embodiment.
Figure 7B:
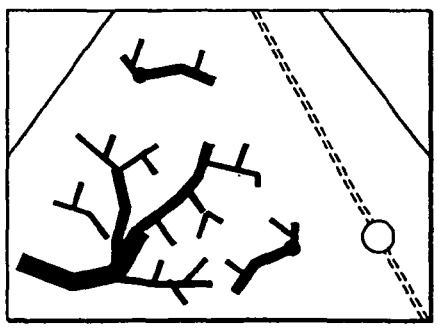
Figure 7C:
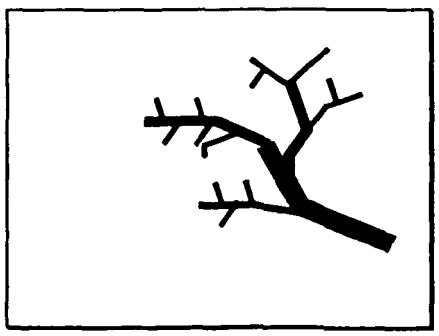

That is, from the brightness value of each pixel constituting the image shown in FIG. 7A, the brightness value of each pixel constituting the image shown in FIG. 7B is subtracted and a difference image illustrated with the dynamic blood state with regard to the blood vessel to which the attention is paid shown in FIG. 7C is generated. The provided difference image is displayed on the monitor 14 (step S17).

Figure 9A:
FIGS. 9A, 9B and 9C are photographs of ultrasonic images acquired by the ultrasonic diagnosis apparatus in accordance with the scan sequence according to the second embodiment.
Figure 9B:
Figure 9C:

Further, FIGS. 9A, 9B, 9C (respectively in correspondence with FIGS. 7A, 7B, 7C) show photographs of the ultrasonic images acquired by the ultrasonic diagnosis apparatus 10 in accordance with the scan sequence according to the embodiment.

According to the above-described sequence, by setting the region of irradiating the ultrasonic wave having the high pressure by the first transmission to a desired position, only the dynamic blood state with regard to the blood vessel present at the region can be extracted. Further, also the blood vessel present outside of the region of irradiating the ultrasonic wave having the high pressure by the first transmission can be extracted as necessary. Therefore, an observer can observe the blood vessel constituting the object of the diagnosis by eliminating information other than the blood vessel and can easily know how the blood stream from the blood vessel to which the attention is paid shows the dynamic blood state.

Further, although according to the above-described operation, the difference operation of the brightness has been adopted as an example, a method which is not limited to the difference can be adopted so far as the method clearly shows the difference between the images G1 and G2. For example, when gray scale brightness values of the image G1 are represented by RGB values, the gray scale brightness values can be represented as (RGB)=(g1, g1, g1) (where notation g1 designates an arbitrary value). Here, when the color of the image G1 is changed as (RGB)=(g1, g1, 0), the gray scale is displayed by the brightness constituting a base tone of yellow color. Similarly, when color tone is changed as (RGB)=(0, 0, g2) in comparison with initial brightness values (RGB)=(g2, g2, g2) of G2, the brightness constituting the base tone by red is displayed. Thereafter, when the images G1 and G2 are subjected to addition processing, an addition image comprising (RGB)=(g1, g1, g2) is provided. According to the addition image, the blood vessel present at the region of irradiating the ultrasonic wave having the high pressure (that is, blood vessel in which the contrast medium is restrained from being supplied by the first transmission) can be identified by the color tone different from that of other portion.

Third Embodiment

As described above, one of the objects of the invention is selective imaging of a region dominated by the certain comparatively large blood vessel. Therefore, with regard to the presented ultrasonic diagnosis image, as shown by, for example, FIG. 7C, it is preferable that the blood flow path is illustrated to be continuously connected from an upstream side to a downstream side of the blood vessel.

In order to realize the illustration, according to the embodiment, brightness holding operation is executing by using image data provided by the method according to the first or the second embodiment. Before explaining the method, a technical background will be explained.

When a next generation type contrast medium is used, according to an investigation by the inventors, a time period of capable of acquiring information in which bubbles of the contrast medium flow into the fine blood vessel branch is about 1 second through 2 seconds from starting recirculation. Thereafter, a signal of an unresolvable capillary level becomes dominant. However, the excellent fine blood vessel branch cannot be illustrated only by displaying an ultrasonic image of a background art during a time period from 1 second through 2 seconds from starting the recirculation. The reason will be explained in reference to FIG. 10 through FIG. 13.

Figure 10:
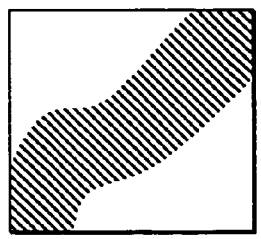
FIG. 10 shows a schematic view of an image representing the blood vessel to which an abundant contrast medium flows.

FIG. 10 shows a schematic view of an image representing the blood vessel in which an abundant contrast medium flows. The abundant contrast medium flows into the comparatively bold blood vessel in this way, and in the case of such a structure of the blood vessel, the continuous blood stream path can be grasped only by the image as shown by FIG. 10. That is, with regard to the comparatively bold blood vessel, the continuous blood stream path can be grasped by the method of the background art. However, with regard to the capillary in which a small amount of the contrast medium flows, the following drawing back is brought about.

Figure 11:
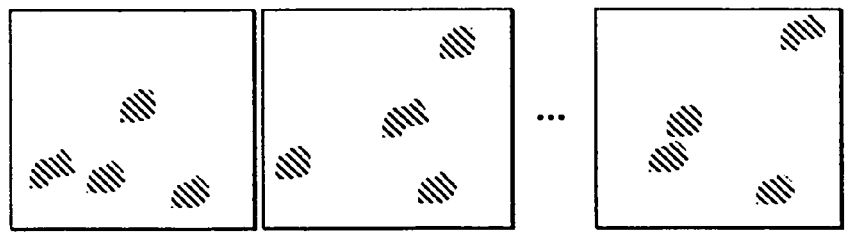
FIG. 11 illustrates schematic views of a plurality of images illustrating the capillaries having small amounts of a contrast medium using a conventional method.

FIG. 11 illustrates schematic views of a plurality of images illustrating the fine blood vessel in which a small amount of the contrast medium flows. As shown by FIG. 11, in the case of the fine blood vessel in which a small amount of the contrast medium flows, bubbles are present only sporadically at an instance in only one sheet of the image and the blood vessel structure cannot be grasped. Further, even by looking at diagnosis images continuously over time, a continuous stream cannot frequently be observed.

Figure 12:
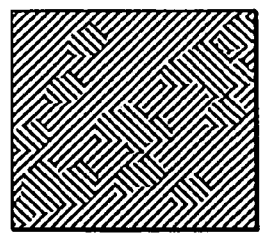
FIG. 12 shows a schematic view of a blood flow image illustrating also a very small blood stream using a conventional method.

Further, FIG. 12 shows a schematic view of a blood flow image illustrating even the small blood flow using a conventional method. According to the image shown by FIG. 12, as described above, the blood vessel branch cannot be illustrated due to a limit in a spatial resolution but only an increase in a brightness as a "region" is confirmed and the fine blood vessel branch cannot be identified.

Figure 13:
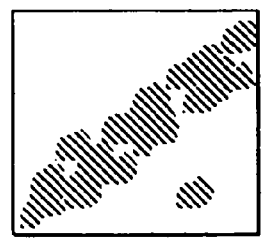
FIG. 13 shows a schematic view of a blood stream image provided by a method according to a third embodiment.

Brightness holding operation executed by the apparatus resolves the problems and enables to provide an image preferably presenting information of a structure (here, blood vessel running network) as one piece of diagnosis information as symbolically shown by FIG. 13.

(Brightness Holding Operation Processing)

An explanation will be given of a brightness holding operation processing provided to the ultrasonic diagnosis apparatus 10. Diagnosis information extracted by the processing includes a blood stream image (including a capillary level) provided by the scan sequence and is useful particularly in illustrating a recirculation image.

The brightness holding operation can be grossly classified by brightness holding operation by a maximum value holding processing and a brightness holding operation by a weighted updating operation. First, an explanation will be given of a maximum value holding processing executed for n sheets of recirculation images of frame $F_1$ to frame $F_n$ included in the same time period $T_L$.

The maximum value holding processing with regard to the images from frame $F_1$ to frame $F_n$ is an operation of generating a new image by selecting a maximum value Pmax (x, y) among spatially correspondent brightness values in respective frames from $F_1$ to $F_n$.

That is, a recirculation image of a certain frame $F_i$ (i is an integer satisfying $1 \leq i \leq n$) comprises a set of spatially arranged brightness values $P_i$ (x, y), or simply a set of a one-dimensional arrangement data $P_i$(x) of brightness values. A value of $P_i$ (x, y) or $P_i$ (x) may be "signal intensity", "signal amplitude", or "live data value of RF data" in place of "brightness", however, the brightness value is adopted here. The respective data values signify that generally, the higher the numerical value, the higher the echo signal level. There is executed operation of generating a new image by selecting a maximum value of the brightness values of respective pixels in spatially corresponding respective frames over frames $F_1$ through $F_n$ by utilizing the respective data values. The operation can be represented by Equation (1) as follows.

$$P_{max}(x, y) = \max [P_1(x, y), \ldots, P_n(x, y)] \quad (1)$$

When the maximum value holding processing is utilized in the recirculation image, at each time of collecting a new frame belonging to the same low sound pressure time period $T_L$, the processing of Equation (1) may be executed and the provided image may be displayed as the recirculation image. The image provided in this way looks to be imaged as a behavior of successively imaging the capillary with elapse of time on the side of the operator (observer).

Further, an algorithm for realizing the maximum value holding processing is not limited to the above-described content. For example, a similar result can be provided by an algorithm, mentioned below.

That is, by designating a pixel brightness of respective coordinates of a current tomographic image frame $F_i$ by notation $P_i$ (x, y) and designating a pixel brightness of a preceding image frame by notation $P_{i-1}$ (x, y), and with regard to two frames relative to each other, an image operation processing represented by the following equations is successively executed until i=2 through n.

If $P_i(x, y) > P_{i-1}(x, y)$ then $P_i(x, y) = P_i(x, y)$

Else $P_i(x, y) = P_{i-1}(x, y)$

According to the algorithm, only a value of a pixel having a brightness value larger than that of an image with regard to a frame at a preceding stage is updated. The operator can observe a behavior of successively imaging the capillary with elapse of time also by the recirculation image provided in this way.

Next, the weighted updating processing will be explained. The weighted updating processing with regard to images from frame $F_1$ through frame $F_n$ generates a new image also by subjecting n sheets of recirculation images from frame $F_1$ through frame $F_n$ included in the same time period of $T_L$ to the weighted updating processing and is an operation represented by the following equations.

If $P_i(x, y) > P_{i-1}(x, y)$ then $P_i(x, y) = A * P_i(x, y) + (1-A) * P_{i-1}(x, y)$ Else $P_i(x, y) = (A-1) * P_i(x, y) + A * P_{i-1}(x, y)$ When the above-described value A is set to a value equal to or smaller than 1 and proximate to 1 (for example, 0.99), there can be expected operation of holding a maximum value of the brightness in a short period of time (in the current case, a time interval from a preceding stage frame) and attenuating the held brightness in a long period of time. The operator can observe a behavior of successively imaging the capillary with elapse of time also by the recirculation image also by such a method.

According to the above-described constitution, by subjecting an image data selectively displaying the blood vessel acquired by the first embodiment and a difference image data acquired by the second embodiment to the brightness holding operation, the fine blood vessel of each image can be illustrated with high resolution and a detailed blood vessel structure can easily and swiftly be grasped.

Further, the invention is not limited to the above-described embodiment as they are, but can be specified by modifying constituent elements thereof within a range not deviated from the gist in an embodying stage.

For example, according to the above-described respective embodiments, the first transmission is defined as "a transmission executed by constituting an object of collapsing bubbles at least a portion of the scanning face, and a transmission constituting an ultrasonic wave of an amount of one frame from, for example, an ultrasonic wave having a low sound pressure to a degree of capable of acquiring a diagnosis image by collapsing bubbles in the scanning face as less as possible and an ultrasonic wave having a high sound pressure to a degree of collapsing bubbles of the contrast medium in the scanning face". In contrast thereto, there may be constructed a constitution of defining the first transmission as "a transmission constituting an ultrasonic wave having a high sound pressure to a degree of collapsing bubbles of the contrast medium only for a region of restraining the contrast medium from flowing in". In this case, in order to realize an effect similar to that in, for example, step S4 shown in FIG. 4 (that is, an effect for acquiring a similar image), the first transmission and the third transmission may alternatingly be repeated.

Further, various aspects of the invention can be formed by pertinently combining a plurality of constituent elements disclosed in the above-described embodiments. For example, a number of constituent elements may be deleted from a total of the constituent elements shown in the embodiments. Further, the constituent elements may pertinently be combined across the different embodiments.

What is claimed is:

1. An ultrasonic diagnosis apparatus which acquires an ultrasonic image by scanning a scan plane in a subject administered with bubbles of a contrast medium by an ultrasonic wave, said ultrasonic diagnosis apparatus comprising:
an ultrasonic probe configured to transmit the ultrasonic wave to the subject and to receive an echo signal from the subject;
a drive signal generating unit configured to generate a drive signal for driving the ultrasonic probe; and
a control unit configured to control the drive signal generating unit to temporally and continuously repeat, for a predetermined period of time, first transmissions to the scan plane to destroy a part of the bubbles of the contrast medium at part of a desired blood vessel and to restrain the contrast medium from flowing into the desired blood vessel in the scan plane, the first transmissions including transmissions of a first ultrasonic wave and transmissions of a second ultrasonic wave, the first ultrasonic wave being transmitted to at least one first predetermined area in the scan plane and having a sound pressure to a degree of not substantially destroying the bubbles of the contrast medium for acquiring a circulation image of a blood stream with regard to the at least one first predetermined area, the second ultrasonic wave being transmitted to a second predetermined area, which does not overlap the at least one first predetermined area in the scan plane, and having a sound pressure to a degree of destroying a part of the bubbles of the contrast medium at part of the desired blood vessel and restraining the contrast medium from flowing into the desired blood vessel during the predetermined period of time.

2. The ultrasonic diagnosis apparatus according to claim 1, wherein the control unit is configured to control the drive signal generating unit to execute second transmissions to the scan plane, the second transmissions including transmissions of an ultrasonic wave having a sound pressure to a degree of destroying the bubbles of the contrast medium for destroying the bubbles of the contrast medium in the scan plane.

3. The ultrasonic wave diagnosis apparatus according to claim 1, wherein the control unit is configured to control the drive signal generating unit to execute third transmissions to the scan plane, the third transmissions including transmissions of an ultrasonic wave having a sound pressure to a degree of not substantially destroying the bubbles of the contrast medium for acquiring a circulation image of a blood stream in the scan plane, the ultrasonic wave diagnosis apparatus further comprising:
an image generating unit configured to generate a difference image or a superposed image of a first ultrasonic wave image provided by the first transmissions and a second ultrasonic wave image provided by the third transmissions.

4. The ultrasonic diagnosis apparatus according to claim 3, wherein the image generating unit is further configured to generate a plurality of frames of ultrasonic wave images by successively executing a brightness value holding operation to generate a plurality difference images by using the first ultrasonic wave images and the second ultrasonic wave images.

5. The ultrasonic diagnosis apparatus according to claim 4, wherein:
the image generating unit is configured to initialize the brightness value holding operation when the third transmissions are executed.

6. The ultrasonic diagnosis apparatus according to claim 5, wherein the brightness value holding operation is a maximum value holding operation for generating the image by selecting a maximum value of the echo signals at a spatially corresponding position in the plurality of frames.

7. The ultrasonic diagnosis apparatus according to claim 3, further comprising:
a storing unit configured to store the first ultrasonic wave image and the second ultrasonic wave image by attaching identifiers respectively capable of identifying the first ultrasonic wave and the second ultrasonic wave image thereto.

8. The ultrasonic diagnosis according to claim 3, further comprising:
a display unit configured to display a region of irradiating an ultrasonic wave having a sound pressure to a degree of destroying the bubbles of the contrast medium when the first transmissions are executed, in the first ultrasonic wave image provided by the first transmissions.

9. The ultrasonic diagnosis apparatus according to claim 3, wherein said image generating unit is further configured to generate a first image of restraining the contrast medium from flowing into the desired blood vessel based on the echo signal provided by the first transmissions and a second image of not restraining the contrast medium from flowing into the desired blood vessel based on the echo signal provided by the third transmissions; and a display unit configured to display an ultrasonic wave image in which a color tone of the desired one of the blood vessel is changed by converting the first image and the second image RGB values of at least one of which is changed.

10. The ultrasonic diagnosis apparatus according to claim 1, further comprising:
an image generating unit configured to generate a plurality of frames of ultrasonic wave images by successively executing a brightness value holding operation based on the echo signals of an amount of a plurality of frames provided by the first transmissions.

11. The ultrasonic diagnosis apparatus according to claim 10, wherein the brightness value holding operation is a maximum value holding operation which generates the image by selecting a maximum value of the echo signals at a spatially corresponding position in the plurality of frames.

12. The ultrasonic diagnosis apparatus according to claim 1, further comprising:
an instructing unit configured to instruct ON/OFF of the first transmissions;
wherein the control unit is configured to control ON/OFF of the first transmissions in response to an instruction from the instructing unit.

13. The ultrasonic diagnosis apparatus according to claim 1, further comprising:
a designating unit configured to designate at least a portion of a transmitted region for restraining the contrast medium from flowing thereinto in the first transmissions.

14. The ultrasonic diagnosis apparatus according to claim 1, further comprising:
an image generating unit configured to generate a plurality of images corresponding to the repeated first transmissions; and
a display unit configured to display time-sequentially a flow of the contrast medium into the desired blood vessel using said plurality of images.

15. A method of controlling an ultrasonic diagnosis apparatus for acquiring an ultrasonic image by scanning a predetermined area in a subject administered with bubbles of a contrast medium by an ultrasonic wave, said method comprising:
generating drive signals for driving an ultrasonic probe for transmitting the ultrasonic wave to the subject and receiving an echo signal from the subject; and
controlling the drive signal generating unit to temporally and continuously repeat, for a predetermined period of time, first transmissions to the scan plane to destroy a part of the bubbles of the contrast medium at part of a desired blood vessel and to restrain the contrast medium from flowing into the desired blood vessel in the scan plane, the first transmissions including transmissions of a first ultrasonic wave and transmissions of a second ultrasonic wave, the first ultrasonic wave being transmitted to at least one first predetermined area in the scan plane and having a sound pressure to a degree of not substantially destroying the bubbles of the contrast medium for acquiring a circulation image of a blood stream with regard to the at least one first predetermined area, the second ultrasonic wave being transmitted to a second predetermined area, which does not overlap the at least one first predetermined area, in the scan plane and having a sound pressure to a degree of destroying a part of the bubbles of the contrast medium at part of a desired blood vessel and restraining the contrast medium from flowing into the desired blood vessel during the predetermined period of time.

16. The method according to claim 15, further comprising:
generating a plurality of images corresponding to the repeated the first transmissions; and
time-sequentially displaying a flow of the contrast medium into the desired blood vessel using said plurality of images.

17. An ultrasonic diagnosis apparatus which acquires an ultrasonic image by scanning a scan plane in a subject administered with bubbles of a contrast medium by an ultrasonic wave, said ultrasonic diagnosis apparatus comprising:
an ultrasonic probe configured to transmit the ultrasonic wave to the subject and to receive an echo signal from the subject;
a drive signal generating unit configured to generate a drive signal for driving the ultrasonic probe; and
a control unit configured to control the drive signal generating unit to repeat first transmissions to the scan plane to destroy a part of the bubbles of the contrast medium at part of a desired blood vessel and to restrain the contrast medium from flowing into the desired blood vessel in the scan plane, the first transmissions including transmissions of a first ultrasonic wave and transmissions of a second ultrasonic wave, the first ultrasonic wave being transmitted to at least one first predetermined area in the scan plane and having a sound pressure to a degree of not substantially destroying the bubbles of the contrast medium for acquiring a circulation image of a blood stream with regard to the at least one first predetermined area, the second ultrasonic wave being transmitted to a second predetermined area, which does not overlap the at least one first predetermined area in the scan plane, and having a sound pressure to a degree of destroying a part of the bubbles of the contrast medium at part of the desired blood vessel and restraining the contrast medium from flowing into the desired blood vessel,
wherein the control unit is configured to control the drive signal generating unit to execute third transmissions to the scan plane, the third transmissions including transmissions of an ultrasonic wave having a sound pressure to a degree of not substantially destroying the bubbles of the contrast medium for acquiring a circulation image of a blood stream in the scan plane, the ultrasonic wave diagnosis apparatus further including
an image generating unit configured to generate a difference image or a superposed image of a first ultrasonic wave image provided by the first transmissions and a second ultrasonic wave image provided by the third transmissions.

* * * * *